United States Patent [19]

Saville

[11] Patent Number: Plant 6,506

[45] Date of Patent: Jan. 3, 1989

[54] ROSE PLANT NAMED SAVALUCK

[75] Inventor: F. Harmon Saville, Rowley, Mass.

[73] Assignee: Nor'East Miniature Roses, Inc., Rowley, Mass.

[21] Appl. No.: 26,280

[22] Filed: Mar. 16, 1987

[51] Int. Cl.[4] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

A new unusual bright orange and yellow bicolor miniature rose.

1 Drawing Sheet

1

The present invention relates to a new and distinct variety of rose plant of the miniature rose class, which was originated by my crossing as seed parent the variety known as "Cheers" (U.S. Plant Pat. No. 5,484) and as pollen parent an unnamed, unpatented seedling of my creation. The denomination of this new rose is "Savaluck".

Among the novel characteristics possessed by this new variety which distinguish it from its parents and all other varieties of which I am aware are its unusual bright orange and yellow bicolored flowers in this class of rose. Flowers are long lasting on the plant and after cutting. Asexual reproduction by budding of the new variety as performed in Essex County, Mass. shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "146C" is plate 146C of The Royal Horticultural Society Colour Chart.

Parentage: Seedling.

*Seed parent.*—"Cheers".

*Pollen parent.*—Unnamed seedling.

Class: Miniature.

The following observations are made of specimens grown outdoors in Essex County, Mass., during the month of September.

FLOWER

Blooming habit: Nearly continuous.

A. Bud:

(1) *Size.*—Medium.

(2) *Form.*—Pointed.

(3) *Color.*—As sepals divide, bud color is near Indian Orange 32A.

(4) *Sepals.*—Relatively smooth, longer than bud.

(5) *Peduncle.*—Length — about one inch. Aspect — straight. Strength — erect. Color — near 146C.

2

B. Bloom:

(1) *Size.*—Average size when fully expanded — about 1¼ to 1½ inches.

(2) *Borne.*—Singly, one to a stem.

(3) *Form.*—High centered at first, becoming flat. Outer petals reflex and quill to points; inner petals roll under.

(4) *Petalage.*—Number of petals under normal conditions — about 24. p2 (5) *Color.*—After sepals fall and petals unfurl, predominant flower color viewing petals' top surface is near 169A through D with flowers varying in color through this range but imbued with yellow underlay producing an overall bright orange color effect. Flowers exhibit deeper toned orange veining and petal edges. Thus, the flower color appears to be the result of yellow and deep toned orange color washing together. The lower segment of petal top surfaces extending toward point of petal attachment appears more distinctly yellow. The petal undersurface is predominantly yellow with some pale orange infusion and veining. Overall tonality from a distance is bright orange.

C. Petals:

(1) *Texture.*—Thick.

(2) *Appearance.*—Inside velvety and outside satiny.

(3) *Form.*—Broad, fan shaped with pointed apices.

(4) *Arrangement.*—Regularly arranged.

(5) *Petaloids in center.*—Few to none.

(6) *Persistence.*—Drop off cleanly.

(7) *Fragrance.*—Slight.

(8) *Lasting quality.*—Very long lasting quality on plant and as cut flower.

REPRODUCTIVE ORGANS

A. Stamens, filaments and anthers:

*Arrangement and color.*—Regularly arranged around styles. Color — filaments near 17B.

B. Pollen:

*Color.*—Near 17A.

C. Styles: Even, medium length, thin.

D. Stigmas:

*Color.*—Near 156C.

E. Hips: None observed.

PLANT

A. Form: Upright, compact.

B. Growth: Vigorous, uniform branching.

*Height attained.*—about 14 to 16 inches.

C. Foliage: Compound 5 to 7 leaflets.

(1) *Size.*—Medium.

(2) *Quantity.*—Abundant.

(3) *Color.*—New foliage: Upper side — near 143A. Under side — near 191A. Old foliage: Upper side — near 147A. Under side —0 near to 148B.

(4) *Shape.*—Oval, pointed.

(5) *Texture.*—Upper side is semiglossy; under side is matte.

(6) *Edge.*—Serrate.

(7) *Serration.*—Ordinary.

(8) *Leaf stem.*—Color — near to 147B. Under side — near 146B.

(9) *Stipules.*—Medium length, slightly bearded.

(10) *Resistance to disease.*—Blackspot — Average. Mildew — Average. Rust — Average.

D. Wood:

(1) *New wood.*—Color — near 137B. Bark — smooth.

(2) *Old wood.*—Color — near 139B. Bark — smooth.

E. Thorns:

(1) *Thorns.*—Quantity (main stalk) — ordinary. On laterals from stalk — few. Form — long, thin, straight, slanted slightly downward. Length — short. Color — near 185A. Position — irregular.

F. Winter hardiness: Needs protection in severe climates.

I claim:

1. A new and distinct variety of rose plant of the miniature rose class, substantially as shown and described, characterized particularly by attractive bright orange and yellow bicolored flowers which are long lasting on the plant and as cut flowers.

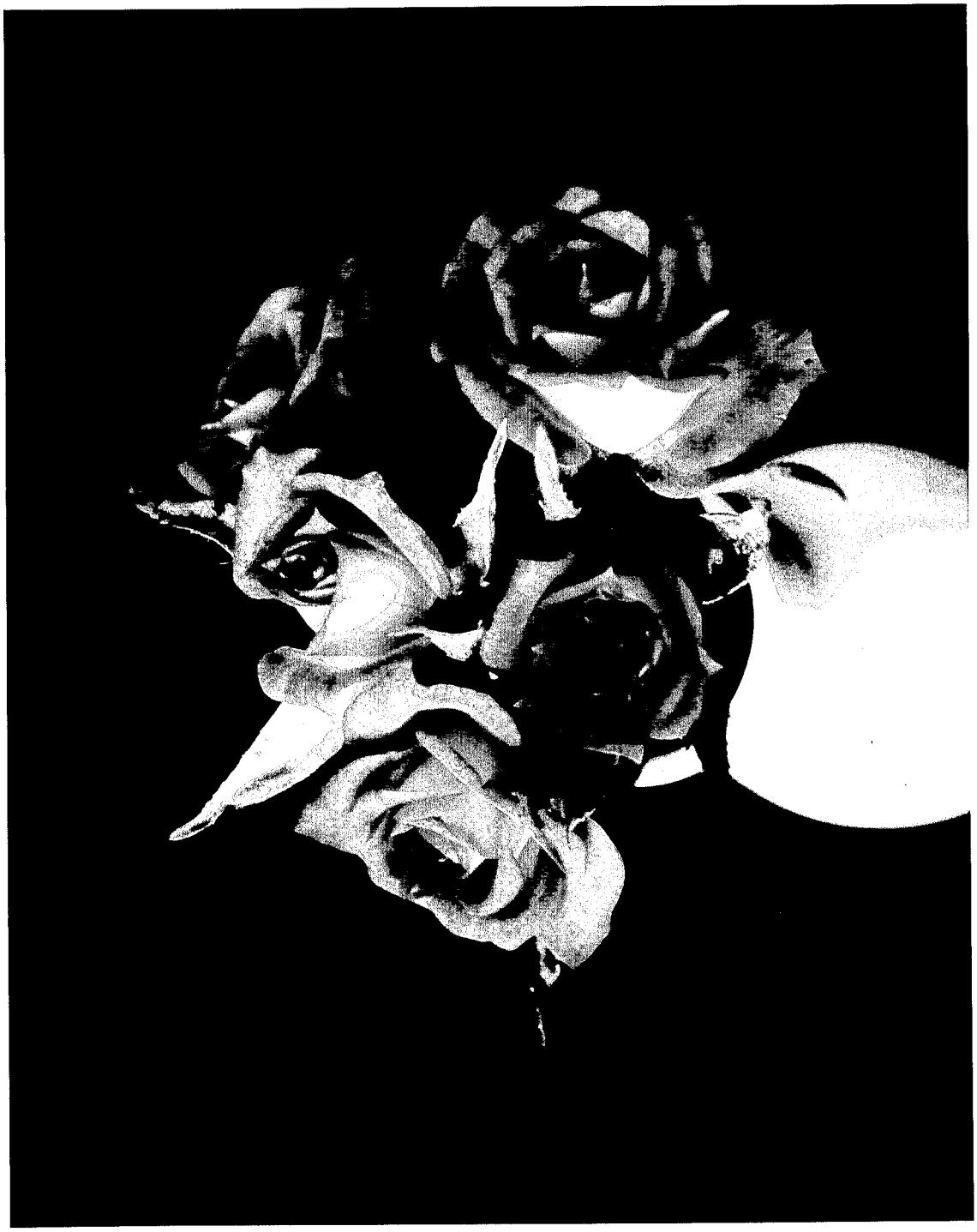

* * * * *